United States Patent [19]

Green et al.

[11] Patent Number: 5,062,563
[45] Date of Patent: Nov. 5, 1991

[54] FASCIA STAPLER

[75] Inventors: David T. Green, Westport, Conn.; Wayne P. Young, Brewster, N.Y.; Henry Bolanos, East Norwalk, Conn.; Robert J. Geiste, Milford, Conn.; Keith Ratcliff, Sandy Hook, Conn.; Daniel E. Alesi, New Fairfield, Conn.

[73] Assignee: United States Surgical Corporation, Norwalk, Conn.

[21] Appl. No.: 335,822

[22] Filed: Apr. 10, 1989

[51] Int. Cl.$^5$ .............................................. A61B 17/00
[52] U.S. Cl. ...................................... 227/176; 227/19; 227/121
[58] Field of Search ................. 227/19, 176, 175, 177, 227/178, 179, 180, 121

[56] References Cited

U.S. PATENT DOCUMENTS

| 4,204,623 | 5/1980 | Green ..................................... 227/19 |
| 4,406,392 | 9/1983 | Campbell et al. ...................... 227/19 |
| 4,448,194 | 5/1984 | DiGiovanni et al. ............ 227/67 X |
| 4,477,007 | 10/1984 | Foslien ............................. 227/121 X |
| 4,506,670 | 3/1985 | Crossley ........................... 227/19 X |
| 4,664,305 | 5/1987 | Blake et al. ...................... 227/121 X |
| 4,887,756 | 12/1989 | Puchy .................................... 227/19 |

Primary Examiner—Paul A. Bell
Attorney, Agent, or Firm—Thomas R. Bremer

[57] ABSTRACT

The fascia stapler has a pistol-shaped housing from which two-piece clips can be ejected for closing an incision. The retainers for the clips and the straps for the clips are held in respective cartridges within the nose of the housing and can be ejected individually upon actuation of the stapler. A pusher assembly within the housing causes an individual strap to be expelled for passage through one end of a strap, piercing through the tissue and securement in the other end of the strap. Approximators with tissue engaging teeth are also used to bunch up the tissue about the incision during a stapling operation.

42 Claims, 8 Drawing Sheets

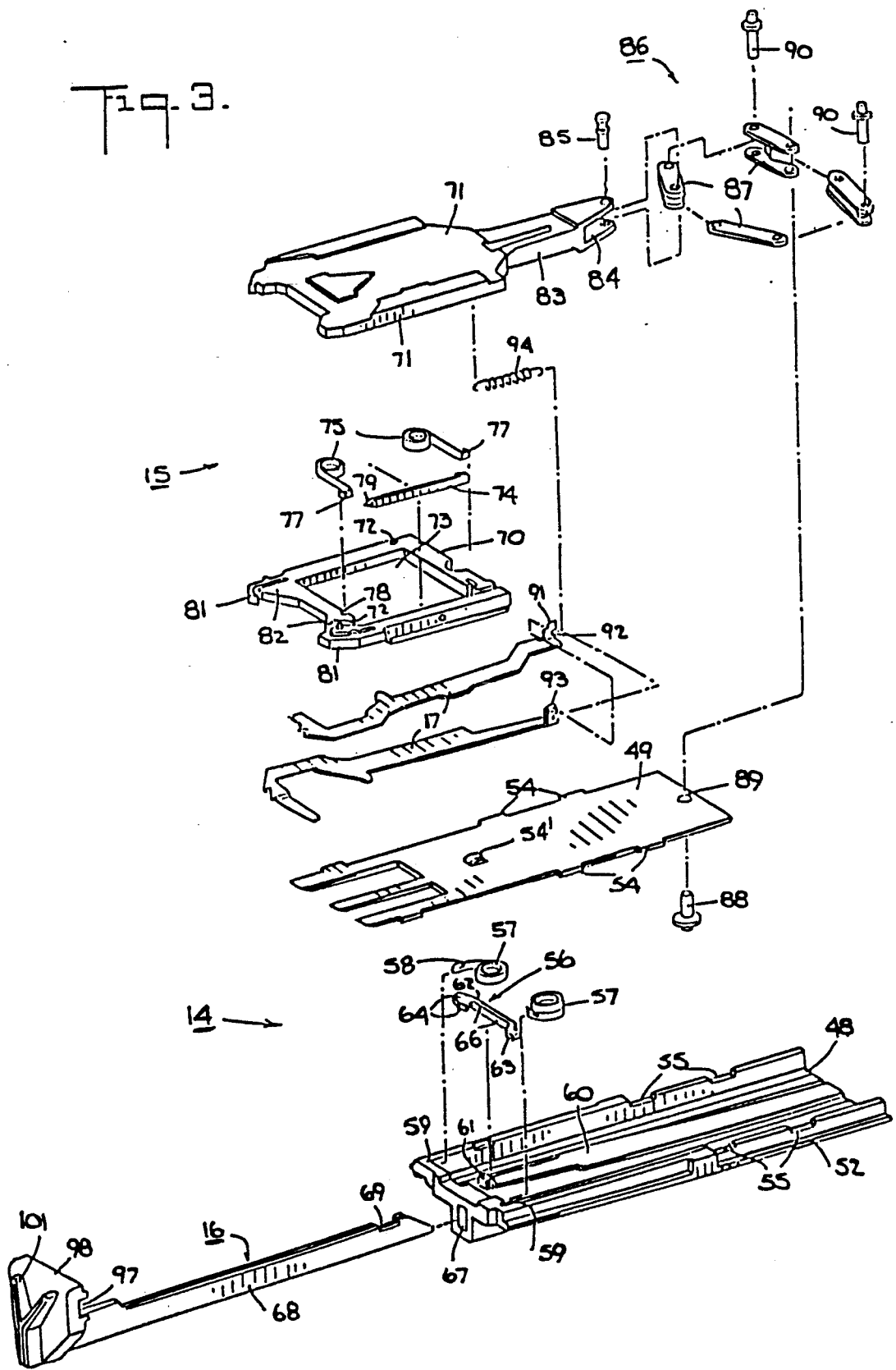

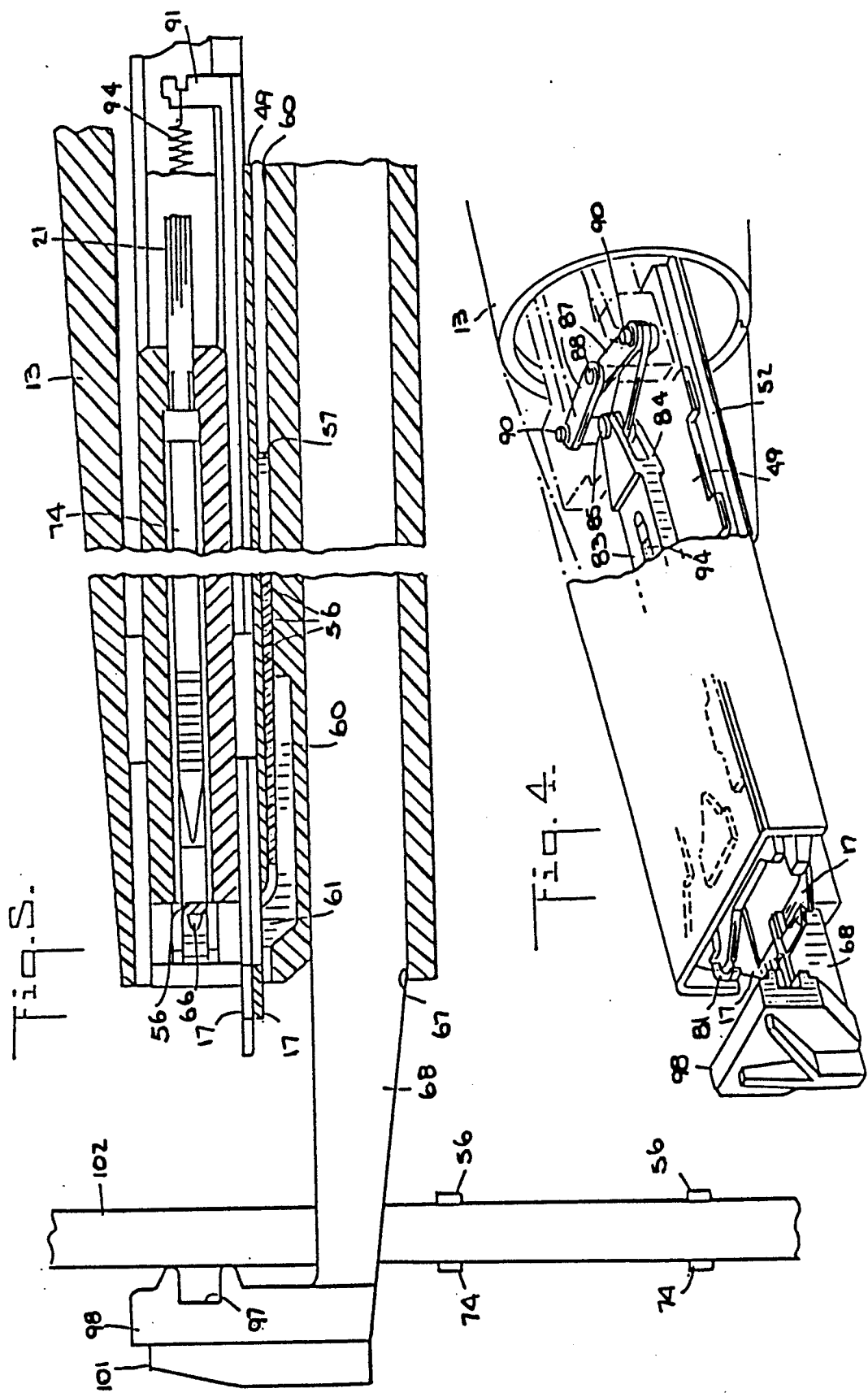

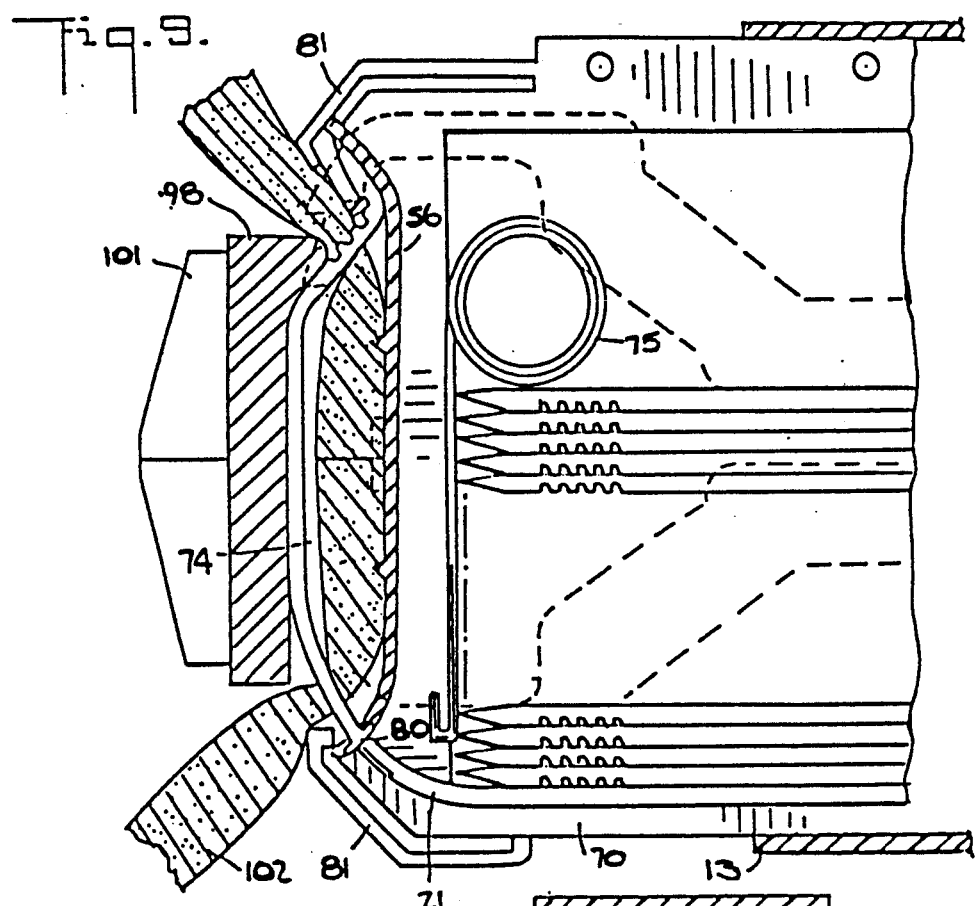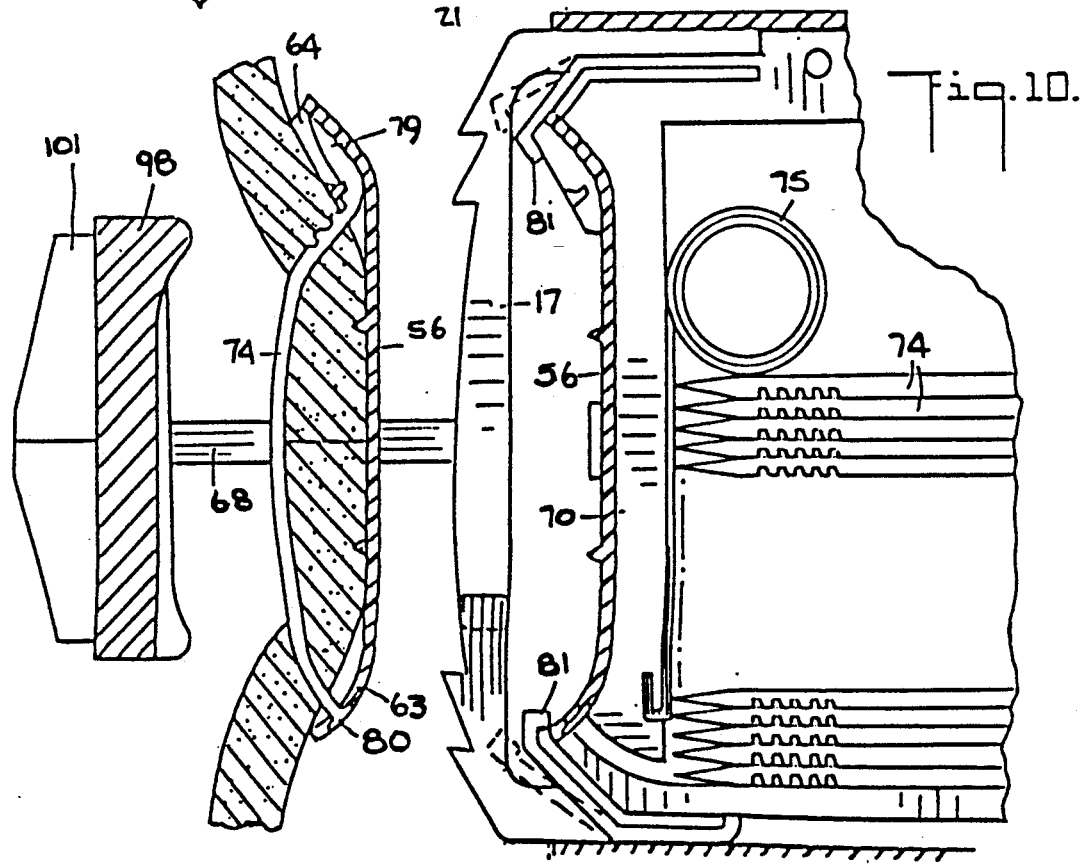

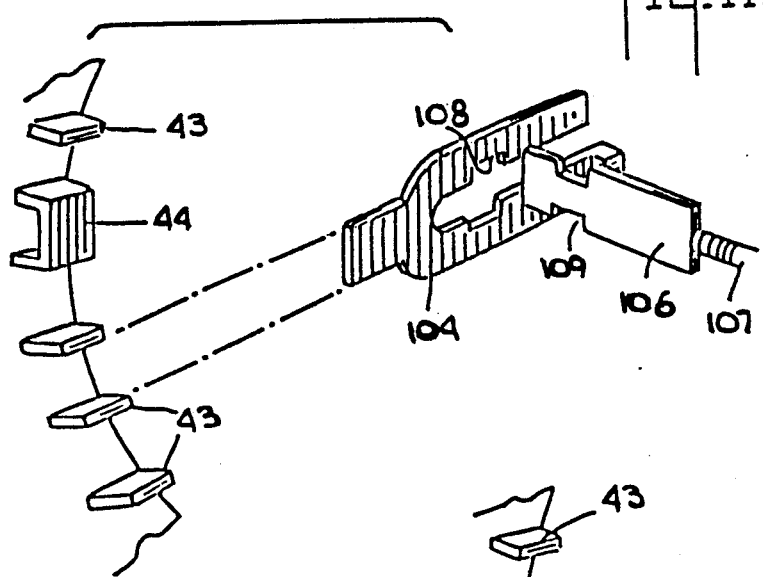
Fig. 11.
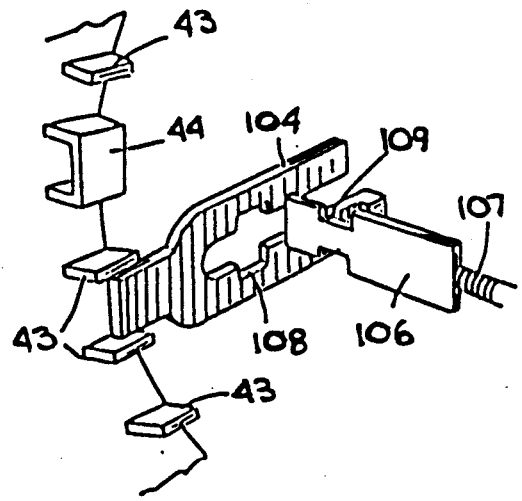
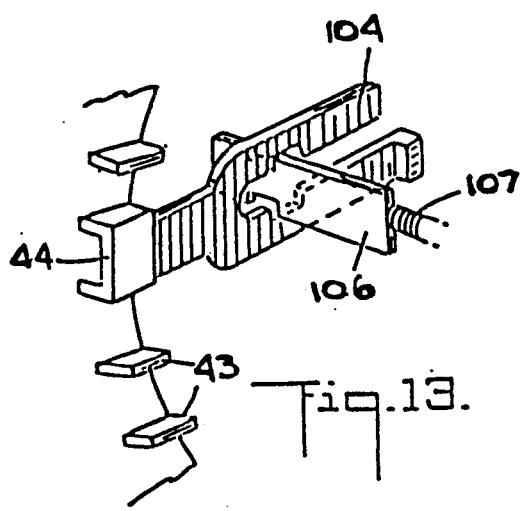
Fig. 12.
Fig. 13.
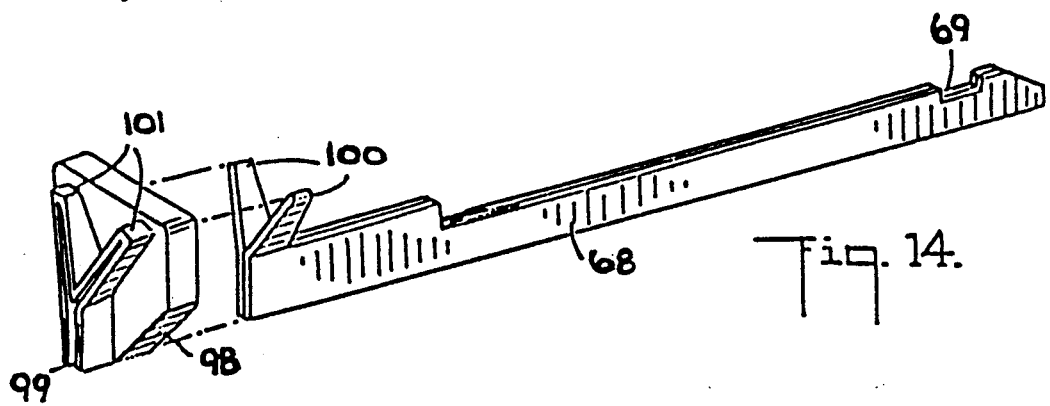
Fig. 14.

FASCIA STAPLER

This invention relates to a fascia stapler. More particularly, this invention relates to a fascia stapler for stapling an incision.

Heretofore, various types of staplers have been used for the stapling of tissue and, particularly, the closing of incisions in the tissue. Generally, these staplers have been constructed so as to eject a generally U-shaped staple into the tissue transverse to the incision while at the same time bending the staple legs towards each other so as to maintain the incision in a closed state. Fascia tissue, however, is relatively thick and not easily manipulated for suturing using conventional stapling techniques.

Accordingly, it is an object of the invention to provide a relatively simple stapler for the stapling of fascia tissue.

It is another object of the invention to provide a stapler capable of rapidly closing an incision in fascia tissue.

It is another object of the invention to provide a fascia stapler which is capable of suturing fascia tissue using fascia staples of two-piece construction.

Briefly, the invention provides a fascia stapler for stapling an incision which includes an anvil which can be inserted under the fascia tissue, a retainer cartridge housing a plurality of elongated retainers and having means for sequentially discharging a foremost retainer, a strap cartridge having a plurality of elongated straps and means for positioning a foremost strap in alignment with the discharge retainer and means for expelling the foremost strap from the strap cartridge in a direction towards the anvil for penetration through the tissue and into engagement with opposite ends of the discharged retainer.

The stapler is constructed so that the foremost retainer can be positioned in spaced parallel relation to the anvil across an incision in the fascia tissue. In addition, the foremost strap is expelled so as to first pass through one end of the positioned retainer and the tissue before being deflected by the anvil across the incision and, thence, through the tissue and the second end of the retainer. In this respect, the strap and retainer form a fascia staple of two-piece construction such as described in pending U.S. patent application Ser. No. 116,627, filed Nov. 3, 1987.

The stapler can be embodied in a pistol-shaped housing from which a rotatable nose projects. In this case, the means for expelling the foremost strap from the strap cartridge for penetration through the tissue includes a plunger which extends into the strap cartridge for pushing the foremost strap therefrom and a pusher which is slidably mounted in the housing and connected to the plunger. In addition, a handle is pivotally mounted on the housing while a linkage is disposed between the handle and the pusher for movement of the pusher in response to pivoting of the handle. In this way, a surgeon may use one hand for firing of a strap from the strap cartridge. Depending upon the mechanical advantage of the linkage, the amount of force required for manual triggering of the stapler can be held to a minimum.

Both the strap cartridge and retainer cartridge are mounted within the nose of the housing along with the anvil so as to be rotated as a unit with the nose. In this way, the anvil and cartridges can be rotated into a position suitable for stapling without having to change the position of the handle for firing purposes.

An articulated linkage is also provided to connect the pusher to the strap cartridge and retainer cartridge for moving the cartridges towards the anvil and out of the housing prior to expelling of the foremost strap. This permits the surgeon to see the positioned retainer prior to expelling of the strap therethrough.

The stapler may also be provided with a pair of movable approximators on opposite sides of the strap cartridge, each of which has a tissue engaging surface for approximating the tissue at the incision. In this case, the approximators are secured to the strap cartridge via a spring means in order to permit relative longitudinal movement therebetween. In use, the strap cartridge with the approximators would first move until the approximators abut the tissue to be stapled. This would be followed by a second movement of the strap cartridge relative to the approximators and then a movement of the foremost strap relative to the strap cartridge and the approximators. In this way, the approximators serve to initially grip the tissue in order to approximate the tissue at the incision followed by the actual stapling operation.

In order to cause the approximators to move towards each other during the relative movement of the strap cartridge, cam surfaces are provided on the strap cartridge to abut the approximators and force the approximators towards each other.

The stapler may also be provided with a counter wheel to indicate the number of staples remaining in the cartridge as well as a lockout assembly to prevent firing of the stapler when empty.

These and other objects and advantages of the invention will become more apparent from the following detailed description taken in conjunction with the accompanying drawings wherein:

FIG. 3 illustrates an exploded view of the strap cartridge, retainer cartridge, anvil, approximators and articulated linkage in accordance with the invention;

FIG. 4 illustrates a partial cut-away perspective view of the components of FIG. 3;

FIG. 5 illustrates a partial cross-sectional view of the front end of the stapler in accordance with the invention;

FIG. 9 illustrates a view similar to FIG. 8 with the foremost strap fired from the strap cartridge;

FIG. 10 illustrates a view similar to FIG. 9 of the stapled incision with the stapler opened and with a strap in place for firing;

FIG. 11 illustrates an exploded view of a lockout assembly to prevent firing of the fascia stapler when empty in accordance with the invention;

FIG. 12 illustrates a view of the lockout assembly in a passive position;

FIG. 13 illustrates a view of the lockout assembly in a blocking position; and

FIG. 14 illustrates a view of an anvil in accordance with the invention.

Figure 1:
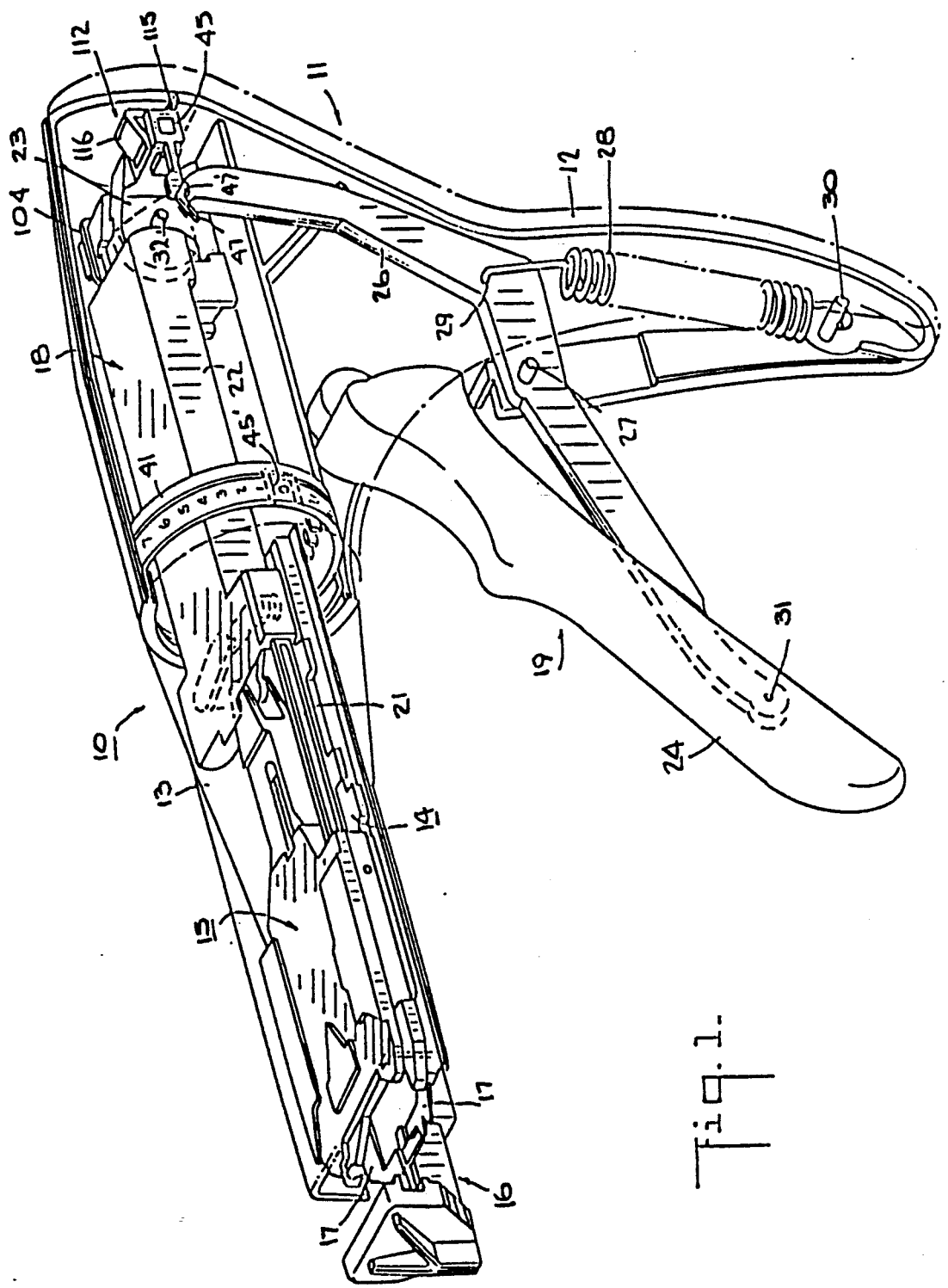
FIG. 1 illustrates a perspective cut-away view of a fascia stapler constructed in accordance with the invention.

Referring to FIG. 1, the fascia stapler (applicator) 10 includes a housing 11 of pistol shape having a L-shaped grip portion 12 and a nose 13 which is rotatably mounted within the grip portion 12. As illustrated, the nose 13 houses a retainer cartridge 14, a strap cartridge 18, an anvil 16 and a pair of approximators 17. In addition, a means is provided for expelling a foremost strap (not shown) from the strap cartridge 15 and includes a pusher assembly 18 and a trigger assembly 19.

Figure 2:
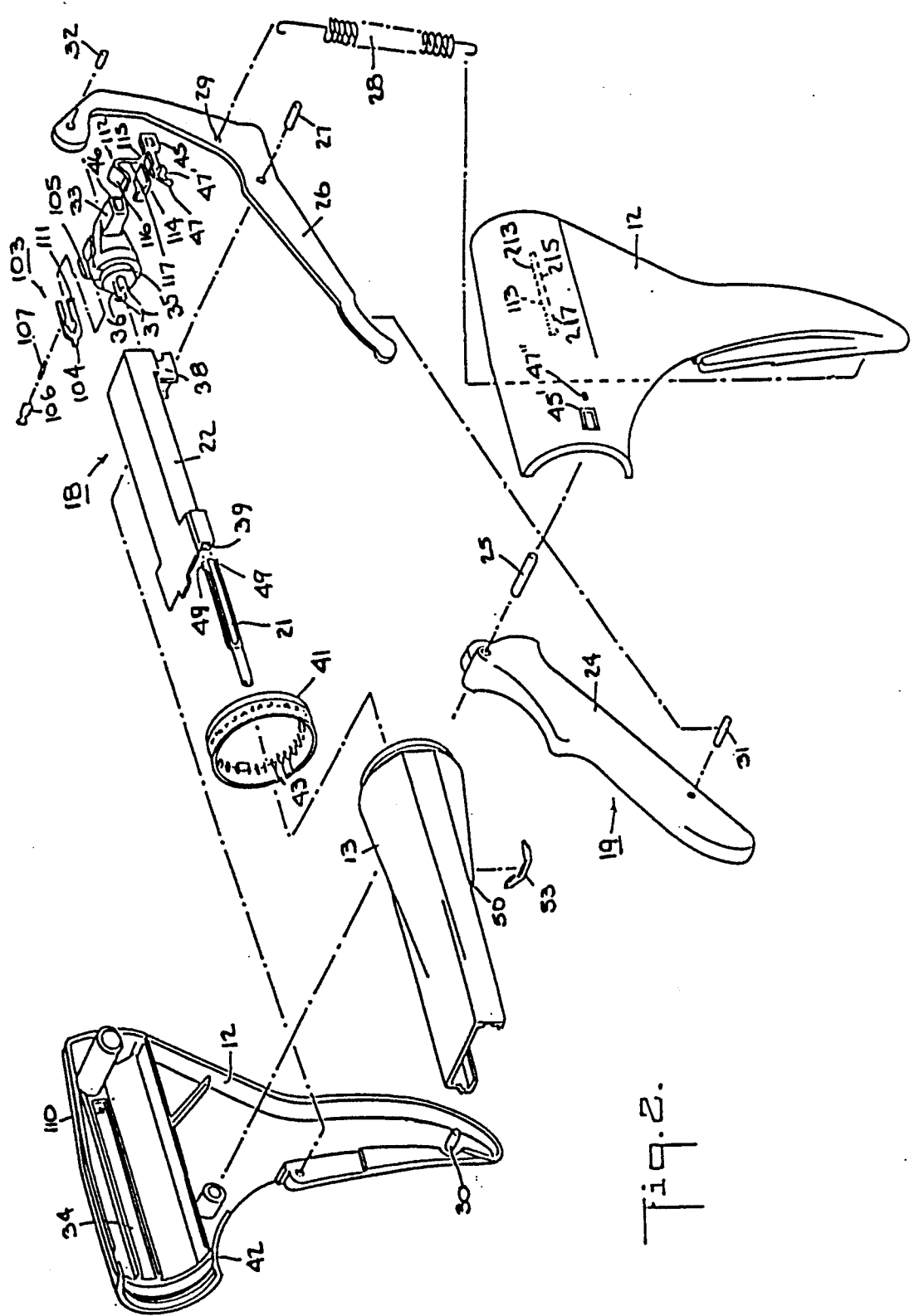
FIG. 2 illustrates an exploded view of the housing and pusher assembly of the stapler in accordance with the invention.

Referring to FIGS. 1 and 2, the pusher assembly 18 includes a plunger 21 which is mounted for sliding within the strap cartridge 15, a pusher 22 connected to the plunger 21 and an adaptor 23 which is connected to the pusher 22 in a manner as to permit rotation of the pusher 22 about a central longitudinal axis of the adapter. In this way, the nose 13 of the stapler 10 can be rotated relative to the grip portion 12 in order to position the anvil 16 and the cartridges 14, 15 relative to the tissue which is to be stapled.

The trigger assembly 19 includes a handle 24 which is pivotally mounted by a pin 25 (FIG. 2) in the grip portion 12 of the housing 11 and a two-armed lever 26 which is pivotally mounted on a pin 27 in the grip portion 12. As indicated in FIG. 1, a return spring 28 is connected between an aperture 29 in one arm of the lever 26 and a fixed pin 30 at the base of the grip portion 12 while a trigger pin 31 in the handle 24 secures the other end of the lever 26 within the handle 24 to permit pivoting therewith. Upon pivoting of the handle 24 towards the grip portion 12, the lever 26 pushes the pusher assembly 18 forwardly towards the anvil 16.

Referring to FIG. 2, wherein like reference characters indicate like parts as above, the grip portion 12 of the housing 11 is of split construction and is held together by the pins 25, 30. Referring to FIG. 2, the lever 26 is secured by a pin 32 at one end to the adapter 23.

The adapter 23 is provided with an outwardly extending block 33 on each side which is slidably received within a longitudinal slideway 34 of a respective half of the grip portion 12. In addition, the adapter 23 has a cylindrical portion 35 which is provided with a bifurcated stem 36 with enlarged heads 37.

The pusher 22 is provided with a flanged portion 38 at the proximal end which has an aperture (not shown) to receive the bifurcated stem 36 of the adapter 23 to secure the pusher 22 to the adapter 23 in rotatable manner. The pusher 22 also includes a longitudinal blind bore 39 at the distal end which receives a proximal end of the plunger 21. Further, the plunger 21 has a serrated proximal end, for example, formed by two pairs of teeth 49 on top and bottom edges for engaging within the bore of the pusher 22 for locking the plunger 21 within the bore 39. The plunger 21 may be of any suitable material, such as a plastic material and has a suitable rigidity for pushing straps from the strap cartridge 15 (see FIG. 1).

Referring to FIGS. 1 and 2, the housing 11 also contains a counter ring 41 which is rotatably mounted in suitable guideways 42 in the distal end of the grip portion 12. As indicated, the counter ring 41 has an internal diameter which permits passage of the pusher 22 therethrough. The counter ring 41 is also provided with a plurality of equispaced tabs 43 which are directed radially inwardly on the inside of the ring 41 as well as a U-shaped block 44 with two legs defining tabs. The number of tabs 43 corresponds to the number of staples within the stapler 10.

The counter wheel 41 cooperates with a means in the form of a lever 45 which is mounted at the end of a block 33 of the adapter 23 for incrementally rotating the wheel 41 in response to movement of the plunger assembly 18 through the wheel 41. For example, the lever 45 has a square aperture which is press fitted over a like-shaped stub 46 projecting from the block 33 and slides within a slideway 34 of the housing 12. As indicated, the lever 45 has a forward end 47 which is angled downwardly, as viewed, so as to engage under a tab 43 of the counter wheel 41. This end 47 carries a cam follower 47' which cooperates with a fixed Cam 47" on the inside wall of the housing 12 adjacent the counter wheel 41. During operation, as the stapler 10 is actuated, the lever 26 pivots counter-clockwise, as viewed in FIG. 1 and moves the adapter 23 with the lever 45 forwardly. As the cam follower 47' on the downwardly angled end 47 of the lever 45 moves under the cam 47" the lever 45 pivots downwardly while moving into the plane of the counter wheel 41. A tab 43 is thus engaged. As the lever 45 continues to move forwardly a slight distance, the cam follower 47' passes by the cam 47" and the downwardly inclined end 47 snaps upwardly causing wheel 41 to rotate, for example, counter-clockwise as viewed in FIG. 2. Upon retraction of the adapter 23, the counter wheel 41 has moved into a position to be subsequently engaged by the lever 45. Of note, the U-shaped block 44 does not impede rotation of the wheel via the lever 45.

Referring to FIG. 2, the housing 11 is provided with a window 45' through which the counter wheel 41 can be viewed. In addition, the counter wheel 41 is provided with a sequence of numbers, for example, from 0 to 20 so that a user may determine the number of staples remaining in the stapler 10. Of note, the indicia may be provided on a label strip which is secured on the counter ring 41.

Referring to FIG. 3, the retainer cartridge 14 includes a molded base 48 and a cover plate 49 which is mounted thereon. The base 48 is sized so as to be secured to the underside of the nose 13 (see FIG. 1). In this respect, the underside of the proximal portion of the nose 13 has a slot 50 (see FIG. 2) in which the base 48 is slidably mounted. In addition, the nose 13 is provided with a pair of longitudinal grooves 51 while the base 48 is provided with splines 52 for sliding into the grooves 51.

Of note, the base 48 may be secured to the nose 13 in a fixed manner, for example by means of a keeper 53 (see FIG. 2) which is mounted in the nose 13 and is able to project at an intermediate part into a mating groove (not shown) in the retainer cartridge 14.

As indicated in FIG. 3, the cover plate 49 has a plurality of tabs 54 which interfit into notches 55 in the base 48 in order to secure the cover plate 49 in place as well as an upstanding tab 54' to act as a stop for limiting the forward motion of the approximators 17.

The retainer cartridge 14 also includes a supply of retainers 56 (only one of which is shown for simplicity), each of which is constructed, for example as described in copending patent application Ser. No. 116,627, filed Nov. 3, 1987. In addition, means are provided for sequentially discharging the retainers 56 from the cartridge 14. As indicated, this means includes a spring assembly formed of a pair of constant force springs 57 which are coiled within the base 48 and secured via a bent-over tab 58 within a slot 59 in the base 48. The springs 57 tend to roll up in order to bias the retainers 56 in the distal direction. In addition, the means for discharging the retainers includes a ramp 60 which is integrally formed within the base 48 and along which the retainers 56 slide. As indicated, the distal end of the ramp 60, is curved upwardly to form a nose 61 so as to cause a retainer 56 moving along the ramp 60 to turn about the longitudinal axis thereof.

Each retainer 56 is of elongated shape and made of a resilient material which may also be absorbable. In addition, each retainer 56 has a main body portion 62, an enlarged proximal end having an opening 63 for passage of a strap and an enlarged distal end having a pair of flanges 64 and a web 65 (see FIG. 6) to form an opening or slot which is sized for passage of a strap. The retainer 56 also has a pair of projections or pins 66 which are shaped and sized to penetrate into fascia tissue on both sides of an incision.

When mounted on the base 48, each retainer 56 is initially disposed with the ends 63, 64 directed downwardly into grooves extending along the base 48, as indicated in FIG. 5. However, the foremost retainer 56 is guided by the curved distal end of the ramp 60 into a position turned 90° therefrom.

The base 48 also includes an elongated sleeve 67 for receiving a stem 68 of the anvil 16. In addition, the underside of the base 48 is provided with a recess (not shown) which receives an anvil pad (not shown) and an anvil stop (not shown) in press fit relation. The anvil stem 68 is provided with a notch 69 which receives a stop and an optional pad. The pad can be made of resilient material and abuts against the proximal end of the notch 69 in the stem 68 while the stop is mounted in a fixed position. The resilience of the pad can permit the anvil 16 to adjust to slightly different thickness of tissue which are to be stapled.

Figure 6:
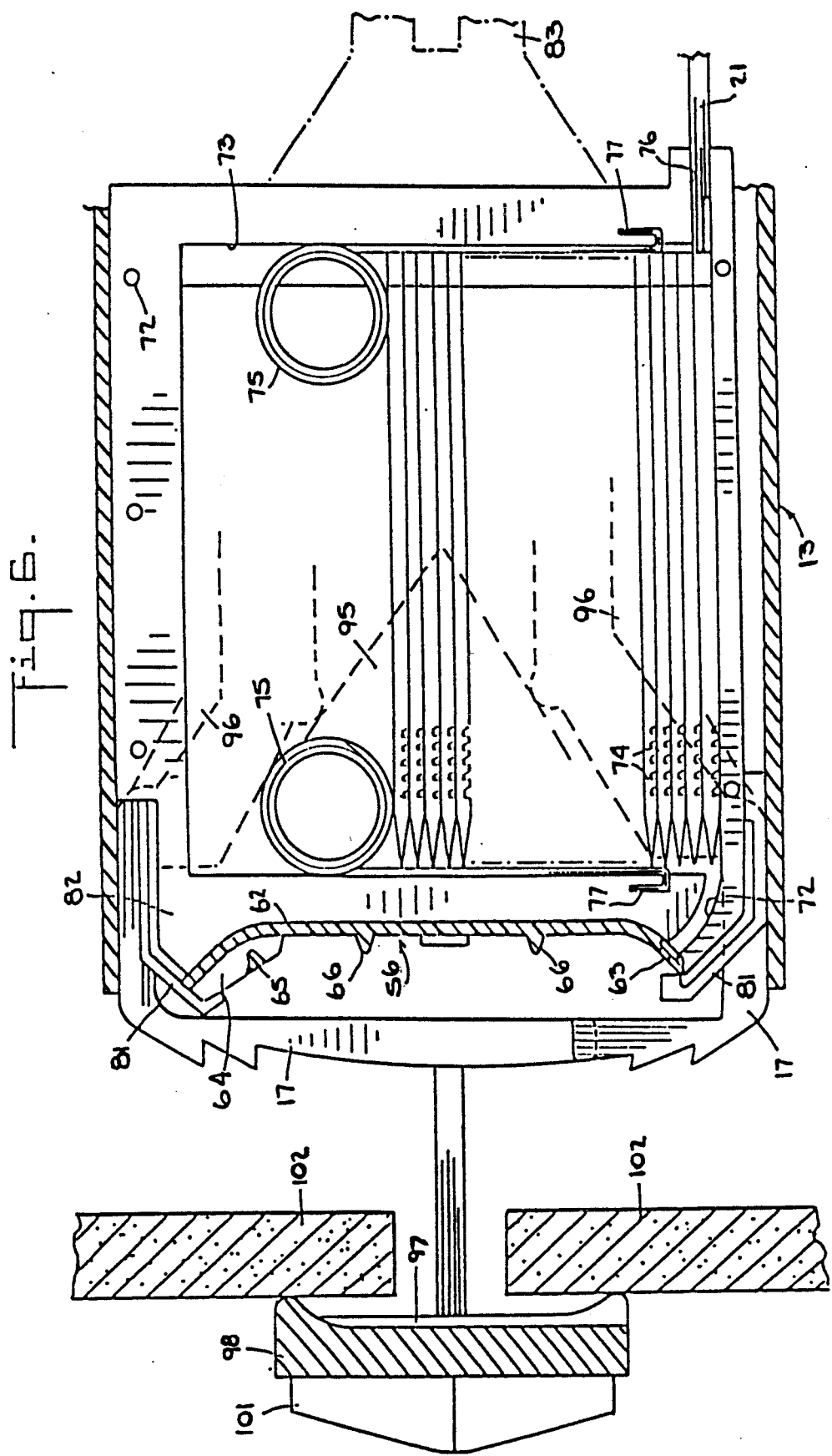
FIG. 6 illustrates a top view of the lower part of the retainer cartridge prior to firing with a strap in place.

Referring to FIG. 3, the strap cartridge 15 includes a transparent plastic base 70 and a plastic cover 71 which are sandwiched together via pins 72 on the base and receiving holes (not shown) in the cover 71. The base 70 is provided with a central recess 73 in which a plurality of straps 74 (only one of which are shown for simplicity) are disposed. In addition, a spring assembly formed of a pair of constant force springs 75 are provided to bias the straps 74 to one side of the base 70 and, in particular, to a longitudinal slot 76. Each spring 75 includes a bent over end 77 which is received within a slot 78 of the base 70 and functions in a manner similar to the springs 57 in the retainer cartridge 14 so as to bias the straps 74 into the slot 76 (FIG. 6). The slot 76, in turn, is aligned with the plunger 21 so as to slidably receive the plunger 21 in abutting relation to a foremost strap within the slot 76.

As illustrated in FIG. 3, each strap 74 is constructed in a manner as described in the above-noted copending patent application. That is, each strap 74 is of a resilient and flexible material with a pointed distal end 79 for passage through the openings 63, 64 in a retainer 56 as well as an enlarged proximal end 80. Each strap 74 may also be provided with a means in the form of resilient teeth at the distal end for engaging with the distal end of a strap 56 in order to prevent withdrawal of the distal end of the strap from the opening 64 in the retainer as described below.

As shown, the distal end of the cartridge base 70 is recessed and is of a shape to receive an expelled retainer 56 from the retainer cartridge 14. In addition, a pair of spring fingers 81 are disposed on opposite sides of the recess in order to resiliently retain a retainer therein. As illustrated in FIG. 6, each spring finger 81 extends over the ends of a retained retainer 56 in order to hold the retainer 56 in place during stapling.

The strap cartridge cover 71 has a pair of abutments 82 which overlie the recess of the cartridge base 70 in order to prevent passage of a retainer 56 thereby. In addition, the cover 71 has an extension 83 at the proximal end having a pair of tabs 84 forming a bifurcated end through which a return pin 85 passes.

An articulated linkage 86 is connected to the pin 85 in order to connect the strap cartridge 15 to the pusher 22 (see FIG. 1). This linkage 86 is formed of a plurality of pivotally connected links 87 which can be moved from an extended position (as indicated in FIG. 3) to a collapsed position. As indicated, one pair of links 87 is pivotally mounted on the pin 85 of the cartridge cover 71 while a second pair of links is mounted on a pin 88 which is fixedly mounted within a bore 89 in the cover plate 49 of the retainer cartridge 14. A suitable retainer clip (not shown) is provided to secure the links 87 to the pin 88. In addition, a pair of rivets 90 secure the foremost links to the rearmost links.

Referring to FIG. 1, each interconnecting rivet 90 of the articulated linkage 86 is received in a cam slot (not shown) within the pusher 22. The cam slots are shaped to initially effect a forward movement of the strap cartridge 15 over the retainer cartridge 14 as the pusher 22 (FIG. 1) moves forwardly. During this time, the articulated linkage 86 moves from the extended position towards a collapsed position, that is, with the rivets 90 moving towards each other. This is due to the fixation of the pin 88 to the cover plate 49 of the retainer cartridge 14 which remains fixed in place. Thereafter, as the rivets 90 move to the inwardmost positions, the slots in the pusher 22 accommodate the rivets 90 while the pusher 22 moves further forward. At this time, the strap cartridge 15 becomes stationary and the plunger 21 moves through the strap cartridge 15.

Referring to FIG. 3, the approximators 17 are mounted on the bottom surfaces of the strap cartridge 15 within grooves (not shown) to move toward and away from each other in scissors-like fashion. One approximator 17 has a raised tang 91 at the proximal end with a slot 92 to receive a raised tab 93 of the other approximator 17 as well as one end of a spring 94 which engages a depending pin (not shown) on the underside of the cover 71. The spring 94 serves to permit a "lost motion" between the approximators 17 and the strap cartridge 15 as described below. The cartridge base 70 is provided with a cam 95 centrally disposed on the bottom side as well as cam surfaces 96 (as indicated in FIG. 6) for biasing the approximators 17. Upon rearward movement of the approximators 17 relative to the strap cartridge 15 due to abutment of the approximators 17 against fascia tissue, the spring 94 elongates and via the cam surfaces 96 brings the approximators 17 towards the central cam 95.

Referring to FIGS. 5 and 6, the anvil 16 is provided with a grooved portion or channel 97 for guiding of a retainer 56 therein as described below.

Referring to FIGS. 3 and 14, the anvil 16 is of two piece construction for assembly purposes. For example, the anvil 16 has a stem 68 of sheet metal which is folded over about a mid-line and a molded plastic head 98 which includes a slot 99 through which the stem 68 passes. In addition, the distal end of the stem 68 is shaped with a pair of ears 100 (FIG. 14) while the head 98 has a pair of flanged portions 101 provided with recesses to accommodate the ears 100 of the stem 68. Thus, in assembling the anvil 16, the stem 68 is slid through the head 98 from left to right as viewed in FIG. 14.

Figure 7:
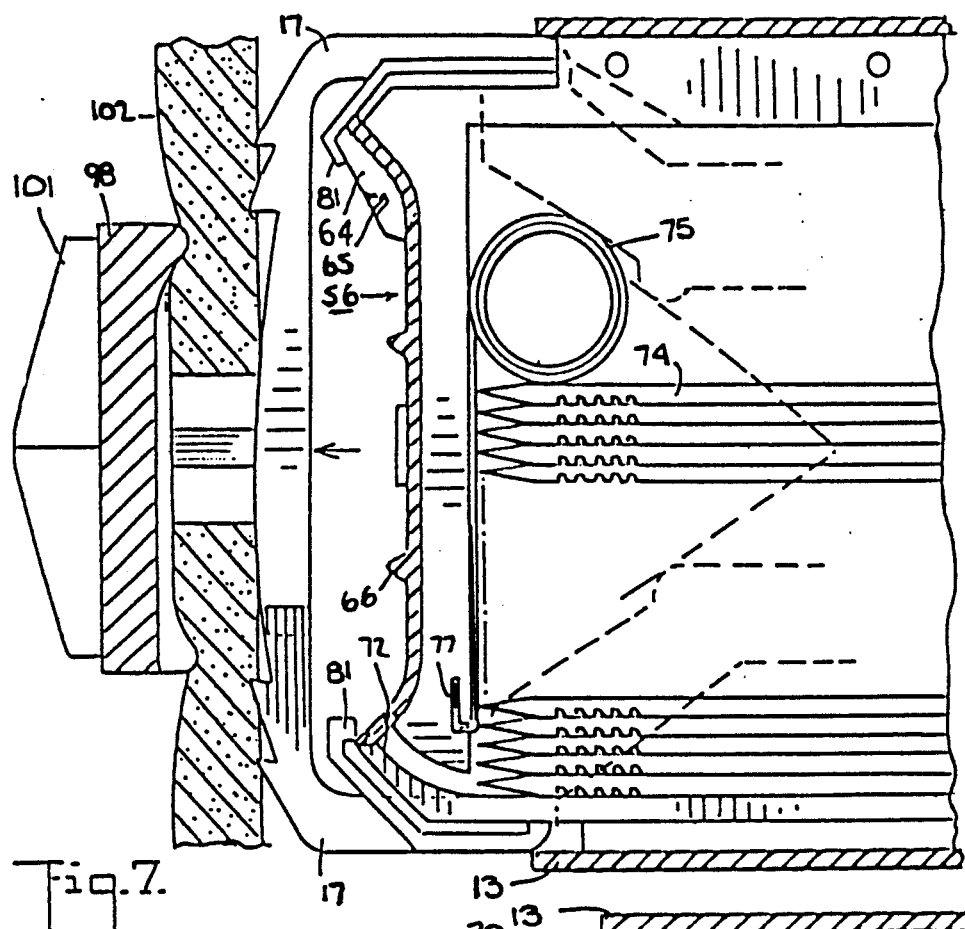
FIG. 7 illustrates a view similar to FIG. 6 with the approximators abutted against the fascia tissue.

In order to use the fascia stapler 10, the anvil 16 is positioned as indicated in FIGS. 5 and 7 within an incision defined by a pair of tissue sections 102. In particular, the anvil 16 is positioned so as to bridge over the incision.

Referring to FIGS. 4 and 5, the fascia stapler 10 is normally delivered in a position with a foremost retainer 56 and foremost strap 74 in place for firing. As illustrated, the strap cartridge 15 is disposed in overlying relation to the retainer cartridge 14 so that the foremost retainer 56 has been expelled into the recess at the forward end of the strap cartridge 15. In this position, the foremost retainer 56 is held in place by the spring fingers 81 (see FIG. 6), the overlying abutments 82 of the strap cartridge cover 71 and, from below, by the nose 61 of the ramp 60. The foremost strap 74 is positioned within the slot 76 of the staple cartridge base 70 and is abutted by the plunger 21.

After positioning of the anvil 16, the handle 24 (see FIG. 1) of the stapler is manually pivoted. This causes the lever 26 to move the pusher assembly 18 forwardly. During a first movement, the approximators 17 are brought into abutment with the tissue 102 on opposite sides of the incision as indicated in FIG. 7. At this time, the distal end of the staple cartridge 15 will have moved beyond the nose 13.

As the pusher assembly 18 continues to move forwardly, the approximators 17 cease further motion forwardly and begin to move inwardly towards each other under the influence of the cam surfaces 96 on the strap cartridge base 70 and the tissue. At the same time, the strap cartridge 15 continues to move forwardly relative to the approximators 17. In this respect, as indicated in FIG. 1, the rivets 90 of the articulated linkage 86 slide inwardly toward each other so that they are a shorter distance apart during the time that the approximators 17 are brought against the tissue. During this time, pins 85 and 88 are moved a further distance apart. Thereafter, the rivets 90 enter angled portions of the cam slots (not shown) to accommodate the relative movement between the strap cartridge 15 and the now stationary approximators 17. Further, during this time, the articulated linkage 86 moves from the extended position into the predetermined collapsed position.

Figure 8:
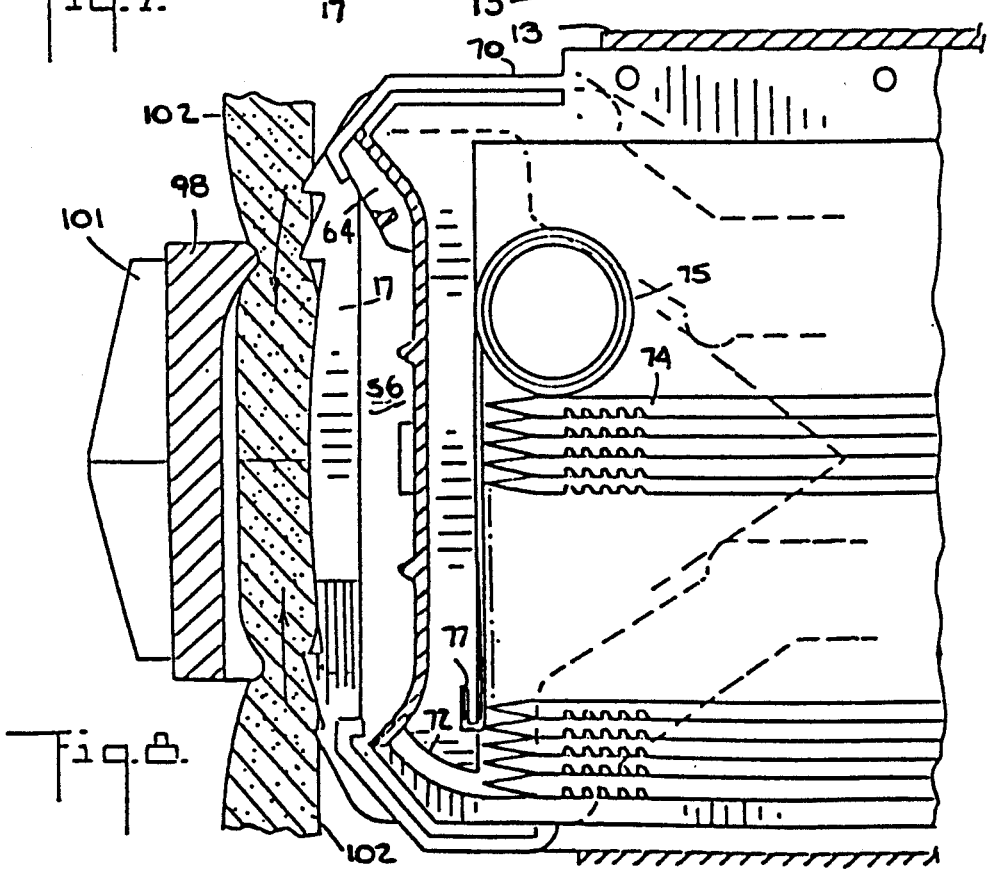
FIG. 8 illustrates a view similar to FIG. 7 with the approximators being moved towards each other and immediately prior to expelling of the foremost strap.

After the strap cartridge 15 has moved against the tissue 102 (FIG. 8) to clamp the tissue, the motion of the cartridge 15 ceases. At this time, the pusher assembly 18 continues to move forwardly so as to push the plunger 21 into the slot 76 of the strap cartridge base 70 causing the forwardmost strap 74 to be expelled, thus firing the stapler. During this time, the pointed distal end of the strap 74 initially passes through the opening 63 of the retainer 56 and then pierces through the layer of tissue 102 to abut the anvil 16. As the strap 74 continues to be pushed, the strap slides within the groove 97 of the anvil 16 so as to pierce through the tissue 102 on the other side of the incision and enter into the opening 64 of the retainer 56 so as to be engaged therein via the rib 65 and teeth of the strap 74.

During the motion of the plunger 21 through the strap cartridge base 70, the articulated linkage 86 remains in the collapsed position i.e. firing position (FIG. 1). In this position, the pusher assembly 18 is free to move relative to the stationary strap cartridge 15.

After the foremost strap 74 has been passed through the tissue 102 into the foremost retainer 56, the handle 24 is in a fully closed position. At this time, the lever 45 will have rotated the counter wheel 41 over an increment equal to the spacing between two tabs 43 with a corresponding change in the number appearing in the window 45'.

Upon release of the handle 24, the spring 28 (FIG. 1) pulls the lever 26 in a clockwise direction, as viewed, so as to pull the pusher assembly 18 rearwardly. This retracts the strap cartridge 15 and the approximators 17 from the stapled incision as indicated in FIG. 10. At this time, the spring fingers 81 of the strap cartridge 15 deflect outwardly to permit outward passage of the retainer 56. During this time also, the next forwardmost retainer 56 in the retainer cartridge 14 is initially held in a position between the ramp 60 and the forward end of the cover plate 49 in the already turned position. As soon as the strap cartridge 15 slides past the forward end of the cover 49, the spring assembly 57 within the retainer cartridge base 48 biases the next foremost retainer 56 into the now overlying recessed portion of the strap cartridge base 70 and another retainer 56 is moved into position between the end of the ramp 60 and the end of the cover 49.

Further operation of the stapler 10 causes subsequent retainers 56 and straps 74 to be expelled so as to further suture the incision in the tissue 102. Prior to a complete closing of the incision, the anvil 16 must be removed and the remainder of the incision sutured in a conventional manner.

Referring to FIG. 2, the stapler 10 includes a lockout assembly 103 to prevent firing of the stapler 10 when empty. This assembly 103 includes a U-shaped trigger 104 which is slidably mounted in a slot 105 of a block 33 of the adapter 23, a bolt 106 which is mounted perpendicular to the trigger 104 within the block 33 and a spring 107 in the block 33 for biasing the bolt 106 outwardly.

As indicated in FIG. 11, the trigger 104 defines a slot of uniform width less than the height of the bolt 106 with an enlarged portion 108 near one end greater than the height of the bolt 106 to permit passage of the bolt 106. In addition, the bolt 106 has an intermediate narrowed portion 109 sized to slide within the slot of the trigger 104 and a distal end sized to project through a window 110 (FIG. 2) in the housing portion 12.

The trigger 104 also has a distal end of a width less than the clear space between adjacent tabs 43 of the counter wheel 41 (FIG. 12) but greater than the spacing between the legs of the block 44 (FIG. 13).

In normal position, the trigger 104 blocks the bolt 106 from movement out of the adapter (FIG. 11).

During operation of the stapler 10, as the adapter 23 moves forward and a staple is fired, the trigger 104 moves into position between two tabs 43 of the counter wheel 43 (FIG. 12). In this position, the bolt 106 remains blocked against movement from the adapter 23. Should, however, the stapler 10 be empty, the U-shaped block 44 of the counter wheel 41 will be in the path of the trigger 104. Hence, should an attempt be made to fire the stapler 10, the trigger 104 will be brought into the position shown in FIG. 13 wherein the block 44 stops movement of the trigger 104. As the adapter 23 continues to move forward relative to the stopped trigger 104, the bolt 106 slides into alignment with the enlarged portion of the slot in the trigger 104 and is sprung therethrough under the bias of the spring 107 into and through the window 110 (FIG. 2) of the housing portion 12. Continued motion of the adapter 23 is, then, prevented and the adapter 23 locked in place. Likewise, the handle 24 of the stapler 10 becomes locked in a closed position.

As indicated in FIG. 2, the trigger 104 carries a raised flange 111 at the proximal end to abut the rear end of the block 33 to preclude movement out of the slot 105.

Referring to FIGS. 1 and 2, the fascia stapler 10 is also provided with a ratchet system to insure that a firing stroke is completed. This ratchet system employs a pawl 112 which is mounted over the block 33 of the adapter 23 and a toothed rack 113 mounted in one half of the grip portion 12 (see FIG. 2). The pawl 112 is in the form of a clip 114, such as a plastic clip, which is slid over the adapter block 33 and held against rotation about the block 33 due to the shape of clip 114. In addition, an integral tab 115 extends rearwardly and downwardly from the clip 114 to engage with the teeth of the rack 113.

During a first stroke, the handle 24 pivots counterclockwise, as viewed, so that lever 26 pushes the pusher assembly 18 forwardly. During this time, the tab 115 of the pawl clip 114 steps over the teeth of the rack 113. Should the handle 24 not complete a first stroke, the pawl tab 115 will remain in engagement with the rack 113 to prevent rearward movement of the pusher assembly 18. At the completion of a firing stroke, the pawl tab 115 will have passed beyond the teeth of the rack 113. The tab 115 then pivots clockwise (e.g. downwardly) slightly while being biased inwardly of the housing 12 by an inclined surface (not shown) at the forward end of the rack 113 so as to lie beside the rack 113. During the return movement of the pusher assembly 18, the tab 115 slides alongside the rack 113 between upper surface 213 and lower surface 215 without engaging with the teeth as it slides along the inside portion of fixed surface. After passing by the rack 113, the tab 115 springs back to the original position for a subsequent firing stroke.

As indicated in FIG. 2, the pawl clip 114 has a top part 116 and a back wall 117 which form a peaked portion spaced from the block 33 so as to flex and accommodate flexing of the tab 115 by the rack 113 during the return stroke of the pusher assembly 18.

The stapler may be constructed so as to be disposable after emptying of one or both of the respective cartridges 14, 15. Alternatively, the stapler may be constructed for re-use. In this respect, the retainer cartridge 14 can be slidably removed from the nose 13. Thereafter, the base 70 of the strap cartridge 15 can be removed from the cover 71 which remains in place. A fresh transparent base 70 filled with straps 71 can then be reinserted in a snap-fit arrangement into the cover 71 and a fresh retainer cartridge 14 can be slid into place.

Of note, the anvil 16 may be adjusted within the retainer cartridge 14 to accommodate different thicknesses of tissue, that is, by moving the stem 68 more or less into the slot 67 and locking the stem in place.

The invention thus provides a fascia stapler of relatively simple construction which can be readily manipulated by a surgeon. Further, the invention provides a fascia stapler by means of which incisions in fascia tissue can be readily closed.

What is claimed is:

1. In a stapler, the combination comprising
   a housing;
   a pusher assembly movably mounted in said housing between a rest position and a fired position;
   a handle articulated to said housing and said pusher assembly for reciprocating said pusher assembly between said positions;
   a toothed rack secured to and within said housing;
   a pawl mounted on said pusher assembly and having a depending tab for selectively engaging said rack during movement of said pusher assembly from said rest position toward said firing position;
   a counter wheel rotatably mounted about said pusher assembly and having a plurality of inwardly directed tabs and a sequence of numbers thereon, and a lever mounted on said pusher assembly for selectively engaging one of said tabs to rotate said wheel in response to movement of said pusher assembly through said wheel.

2. The combination as set forth in claim 1 which further comprises a cam on said housing adjacent said counter wheel and a window in said housing for viewing said counter wheel and wherein said lever has a cam following thereon for engaging said cam to deflect said lever under a tab of said counter wheel during movement of said lever towards said counter wheel.

3. A fascia stapler for stapling an incision comprising an anvil;
   a retainer cartridge housing a plurality of elongated retainers and having means for sequentially discharging said retainers therefrom into spaced parallel relation to said anvil for disposition across an incision;
   a strap cartridge housing a plurality of flexible elongated straps and having means for positioning a foremost strap in alignment with one end of a discharged retainer from said cartridge; and
   means for expelling said foremost strap from said strap cartridge in a direction towards said anvil for penetration through the tissue and into engagement with opposite ends of said discharged retainer.

4. A stapler as set forth in claim 3 wherein said means in said retainer cartridge includes a spring assembly biasing said retainers in a direction out of said retainer cartridge and a leaf spring for directing a foremost retainer out of said retainer cartridge.

5. A stapler as set forth in claim 4 wherein said strap cartridge is positioned in overlying relation to said retainer cartridge and includes means for receiving said foremost retainer in alignment with said foremost strap.

6. A stapler as set forth in claim 5 wherein said means for expelling said foremost strap from said strap cartridge includes a reciprocally mounted plunger for pushing said foremost strap from said strap relation.

7. A stapler as set forth in claim 6 wherein said means for expelling said foremost strap includes a pusher assembly having a pusher abutting said plunger, a pivotally mounted handle for triggering said pusher assembly and a linkage between said handle and said pusher assembly.

8. A stapler as set forth in claim 7 which further comprises a housing said linkage and said pusher assembly and having said handle pivotally mounted thereon and a nose rotatably mounted on said housing and housing said cartridges therein.

9. A stapler as set forth in claim 3 wherein said anvil includes a mounting shaft mounted in said retainer cartridge.

10. A stapler as set forth in claim 3 wherein said strap cartridge is positioned in overlying relation to said retainer cartridge and includes means for receiving said foremost retainer in alignment with said foremost strap.

11. A stapler as set forth in claim 3 wherein said means for expelling said foremost strap from said strap cartridge includes a reciprocally mounted plunger for pushing said foremost strap from said strap relation.

12. A stapler as set forth in claim 11 wherein said means for expelling said foremost strap includes a pusher assembly having a pusher abutting said plunger, a pivotally mounted handle for triggering said pusher assembly and a linkage between said handle and said pusher assembly.

13. A stapler as set forth in claim 12 further comprising a counter wheel rotatably mounted about said pusher assembly and having a plurality of inwardly directed tabs and a sequence of numbers thereon, and a lever mounted on said pusher assembly for selectively engaging one of said tabs to rotate said wheel in response to movement of said pusher assembly through said wheel.

14. A stapler as set forth in claim 13 further comprising a lockout assembly to lock said pusher assembly in place in response to said staple cartridges being empty.

15. A stapler as set forth in claim 3 which further comprises at least one pair of movably mounted approximators having tissue engaging surfaces for positioning on opposite sides of an incision and means for moving said approximators toward each other prior to expelling of said foremost strap to approximate the tissue about the incision.

16. A stapler as set forth in claim 15 wherein said approximators are mounted on said strap cartridge.

17. A stapler as set forth in claim 16 wherein said means for expelling said foremost strap includes a reciprocally mounted pusher and which further comprises an articulated linkage connecting said pusher to said strap cartridge for moving said strap cartridge towards said anvil prior to expelling of said foremost strap.

18. A stapler as set forth in claim 17 which further comprises spring means securing said approximators to said strap cartridge to permit relative longitudinal motion therebetween during movement of said strap cartridge towards said anvil.

19. A stapler as set forth in claim 18 wherein said strap cartridge has cam surfaces thereon for moving said approximators towards each other during relative movement between said approximators and said strap cartridge.

20. A fascia stapler comprising
a housing having a nose extending therefrom;
a retainer cartridge mounted in said nose with a plurality of elongated retainers therein and means for discharging a foremost retainer for disposition across an incision;
a strap cartridge mounted in said nose with a plurality of elongated straps therein and having means for positioning a foremost strap in alignment with said foremost retainer;
an anvil extending from said nose in opposition to said cartridges; and
means in said housing for expelling said foremost strap from said strap cartridge in a direction towards said anvil for penetration through the tissue and into engagement with opposite ends of said discharged retainer.

21. A stapler as set forth in claim 20 wherein said means for expelling said foremost strap includes a plunger extending into said strap cartridge and a pusher slidably mounted in said housing and connected to said plunger.

22. A stapler as set forth in claim 21 which further comprises an articulated linkage connecting said pusher to said strap cartridge for moving said strap cartridge towards said anvil prior to expelling of said foremost strap.

23. A stapler as set forth in claim 22 wherein said pusher includes a pair of cam slots therein and said articulated linkage includes a pair of rivets, each said rivet being slidably mounted in a respective slot and said slots being shaped to effect a first movement of said strap cartridge relative to said retainer cartridge and a second movement of said foremost strap relative to said strap cartridge.

24. A stapler as set forth in claim 23 wherein said strap cartridge is positioned in overlying relation to said retainer cartridge and includes means for receiving said foremost retainer in alignment with said foremost strap.

25. A stapler as set forth in claim 22 which further comprises a pair of movably mounted approximators mounted on one side of said strap cartridge, each approximator having a tissue engaging surface projecting beyond said strap cartridge and spring means securing said approximators to said strap cartridge to permit relative longitudinal movement therebetween.

26. A stapler as set forth in claim 25 wherein said pusher includes a pair of cam slots therein and said articulated linkage includes a pair of rivets, each said rivet being slidably mounted in a respective slot and said slots being shaped to effect a first movement of said strap cartridge with said approximators, a second movement of said strap cartridge relative to said approximators and a third movement of said foremost strap relative to said strap cartridge and said approximators.

27. A stapler as set forth in claim 26 wherein said articulated linkage is movable between an extended position and a collapsed position.

28. A stapler as set forth in claim 25 wherein said strap cartridge has cam surfaces thereon for moving said approximators towards each other during relative movement between said approximators and said strap cartridge.

29. A stapler as set forth in claim 21 wherein said means for expelling said foremost strap includes a handle pivotally mounted on said housing and a linkage between said handle and said pusher for moving said pusher in response to pivoting of said handle.

30. In a fascia stapler, the combination comprising
a retainer cartridge housing a plurality of elongated retainers and having means for sequentially discharging a foremost retainer therefrom;
a strap cartridge having a plurality of elongated straps and having means for positioning a foremost strap in alignment with said discharged retainer; and
means for expelling said foremost strap from said strap cartridge into engagement with opposite ends of said discharged retainer.

31. The combination as set forth in claim 30 wherein said strap cartridge is positioned in overlying relation to said retainer cartridge and includes means for receiving said foremost retainer in alignment with said foremost strap.

32. The combination as set forth in claim 30 wherein said means for expelling said foremost strap includes a plunger extending into said strap cartridge and a slidably mounted pusher connected to said plunger.

33. The combination as set forth in claim 32 which further comprises an articulated linkage fixedly mounted on said retainer cartridge and articulated to and between said pusher and said strap cartridge to effect a first movement of said strap cartridge relative to said retainer cartridge and a second movement of said foremost strap relative to said strap cartridge.

34. The combination as set forth in claim 30 which further comprises a pair of movably mounted approximators mounted on opposite sides of said strap cartridge, each approximator having a tissue engaging surface projecting beyond said strap cartridge and spring means securing said approximators to said strap cartridge to permit relative longitudinal movement therebetween.

35. The combination as set forth in claim 34 which further comprises an articulated linkage fixedly mounted on said retainer cartridge and articulated to and between said pusher and said strap cartridge to effect a first movement of said strap cartridge with said approximators thereon, a second movement of said strap cartridge relative to said approximators and a third movement of said foremost strap relative to said strap cartridge.

36. The combination as set forth in claim 30 wherein said means includes a slidably mounted pusher assembly having a plunger extending into said strap cartridge for expelling the foremost strap.

37. The combination as set forth in claim 36 which further comprises a handle articulated to said pusher assembly for reciprocating said pusher assembly relative to said strap cartridge, a counter wheel rotatably mounted about said pusher assembly and having a sequence of numbers thereon and means on said pusher assembly for incrementally rotating said wheel in response to movement of said pusher assembly through said wheel.

38. The combination as set forth in claim 37 wherein said wheel has a plurality of radially inwardly directed tabs and said means on said pusher assembly includes a lever having an angled end for sequentially abutting said tabs to rotate said wheel in response to repeated movements of said pusher assembly through said wheel.

39. The combination as set forth in claim 38 which further comprises a housing containing said pusher assembly and having a cam adjacent said counter wheel, and wherein said lever has a cam following thereon for engaging said cam to deflect said lever under a tab of said counter wheel during movement of said lever towards said counter wheel.

40. The combination as set forth in claim 37 further comprising a lockout assembly mounted on said pusher assembly for abutting said counter wheel in a position corresponding to an empty stapler to lock said stapler against firing.

41. The combination as set forth in claim 40 wherein said lockout assembly includes a trigger for abutting said wheel in said position and having an opening therein, a bolt disposed perpendicularly of said trigger and sized to pass through said opening in said position and a spring biasing said bolt through said opening.

42. The combination as set forth in claim 41 further comprising a housing containing said pusher assembly and having a window for receiving said bolt in said empty position of said stapler.

* * * * *